United States Patent [19]

Lovegrove

[11] Patent Number: 4,618,409
[45] Date of Patent: Oct. 21, 1986

[54] ELECTROPHORETIC SEPARATOR

[75] Inventor: Peter C. Lovegrove, Didcot, England

[73] Assignee: United Kingdom Atomic Energy Authority, London, England

[21] Appl. No.: 691,001

[22] Filed: Jan. 14, 1985

[30] Foreign Application Priority Data

Jan. 20, 1984 [GB] United Kingdom ................. 8401510

[51] Int. Cl.⁴ ............................................. G01N 27/28
[52] U.S. Cl. ............................ 204/300 R; 204/299 R; 204/180.1; 204/275; 204/272
[58] Field of Search ............ 204/300 R, 299 R, 180.1, 204/275, 272

[56] References Cited

U.S. PATENT DOCUMENTS

| 1,551,672 | 9/1925 | Knollenberg | 138/44 |
| 3,387,348 | 6/1968 | Kilgallon | 425/110 |
| 3,616,453 | 10/1971 | Philpot | 204/299 R |
| 3,844,926 | 10/1974 | Smyth et al. | 204/299 R |
| 4,149,957 | 4/1979 | Gibson et al. | 204/300 R X |
| 4,233,146 | 11/1980 | Rothmayer et al. | 204/301 X |
| 4,465,583 | 8/1984 | Lovegrove | 204/299 R |

FOREIGN PATENT DOCUMENTS 310267 1/1919 Fed. Rep. of Germany .

Primary Examiner—John F. Niebling
Assistant Examiner—B. J. Boggs, Jr.
Attorney, Agent, or Firm—William R. Hinds

[57] ABSTRACT

A continuous flow electrophoretic separator 10 comprises a cylindrical stator 12 and a tubular rotor 14 defining an annular chamber 28 therebetween, through which a carrier liquid 44 is passed and in which electrophoresis of a migrant material injected into the carrier liquid 44 takes place. An inlet for the migrant material is defined within the stator 12 and comprises a supply duct 34, a first annular chamber 140, a second annular chamber 144, a peripheral slot 150, ducts 134 providing communication between the supply duct and the first chamber, and channels 142 providing communication between the first chamber and the second chamber. Migrant material flows from the second chamber through the slot to emerge uniformly into the carrier liquid as a well defined narrow layer.

7 Claims, 4 Drawing Figures

ELECTROPHORETIC SEPARATOR

This invention relates to a continuous flow electrophoretic separator, and in particular to an inlet means therefor.

A continuous flow electrophoretic separator comprises a cylindrical stator, a concentric tubular rotor defining an annular chamber between the stator and the rotor, an electrode incorporated in the stator, an electrode incorporated into the rotor, means for causing a carrier liquid to flow through the chamber, and an inlet means in the stator for injecting a migrant material into the carrier liquid. In operation, an electric field is applied radially across the annular chamber between the electrodes, carrier liquid is caused to flow through the annular chamber, and the rotor is rotated about the stator so as to stabilise laminar flow in the chamber. Migrant material injected into the carrier liquid is thus subjected to electrophoretic separation.

An example of a continuous flow electrophoretic separator is described in UK Patent Specification No. 1,186,184 (U.S. Pat. No. 3,616,453), and modifications to that example are described in UK Patent Specifications Nos. 1,431,888 and 1,431,887 (U.S. Pat. No. 3,844,926), and in UK No. 1,578,809 (U.S. Pat. No. 4,149,957). Such separators may be used to fractionate an inlet stream into a plurality of outlet streams.

UK Pat. No. 1,431,887 describes a continuous flow electrophoretic separator wherein the inlet means includes a porous material through which the migrant material is constrained to flow. This provides a smooth and even flow of migrant flow into the carrier liquid. However it is difficult to clean such a porous material, so that such an inlet means is not suitable where the migrant material includes cells or large biologically-active molecules.

According to the present invention there is provided a continuous flow electrophoretic separator as hereinbefore defined, having a substantially cylindrical stator including an inlet means for a migrant material, the inlet means comprising:
a supply duct for the supply of the migrant material,
a first annular chamber,
a plurality of ducts providing communication between
the supply duct and the first annular chamber,
a circumferential slot around the periphery of the stator,
a second annular chamber coaxial with the stator and in fluid communication with the slot,
and a plurality of channels providing fluid communication between the first annular chamber and the second annular chamber,
so that in use the flux of the migrant material is substantially the same through all parts of the slot.

Desirably the number of channels is at least twice the number of ducts, and the channels and the ducts are equally spaced, none of the channels being aligned with the ducts. The ducts and the channels may extend in radial directions and may lie in planes perpendicular to the axis of the stator. The slot may also lie in a plane perpendicular to the axis of the stator, and desirably is not aligned with the channels.

The inlet means may be fabricated in a rigid plastics material, or even in a metal such as stainless steel, which is surprising in view of the proximity of the inlet means to the electrodes of the separator.

The invention will now be further described by way of example only and with reference to the accompanying drawings, in which.

Figure 1:
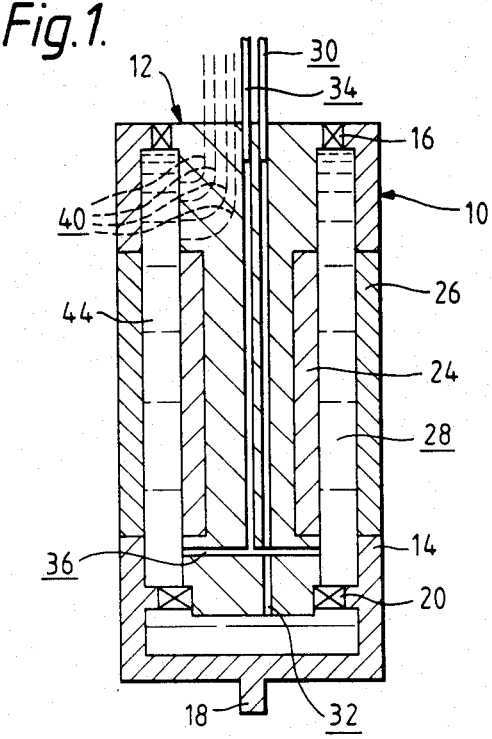
FIG. 1 is a diagrammatic medial sectional representation of an electrophoretic separator.

Referring to FIG. 1, an electrophoretic separator 10 is shown similar in principle to those described in the aforementioned patent specifications. The separator 10 comprises a rigidly mounted cylindrical stator 12, and a concentric tubular rotor 14 rotatably connected to the stator 12 by a bearing 16 at its upper end and drivable by means of a stub shaft 18 attached to the lower end of the rotor 14. The lower end of the stator 12 is spaced apart from the rotor 14 by a bearing 20 through which liquid is free to flow. The stator 12 incorporates a cylindrical electrode 24 along a portion of its length, and the rotor 14 incorporates a tubular electrode 26 in opposed relationship to the electrode 24 so as to define an annular chamber 28 between the two electrodes 24 and 26 in which, in operation of the separator 10, electrophoresis takes place. A duct 30 extends through the stator 12 to a port 32 at the lower end of the stator 12, and a duct 34 extends through the stator 12 to communicate with a slot 36 around the perimeter of the stator 12 below the lower end of the electrode 24. Thirty discharge ducts 40 (only four of which are indicated by broken lines) extend through the stator 12 from thirty axially displaced positions on the surface of the stator 12 above the upper end of the electrode 24. For further details with respect to the construction of the electrophoretic separator 10 reference is directed to the aforementioned specifications.

In operation of the separator 10, a potential difference is applied between the two electrodes 24 and 26 so as to set up a radial electric field across the annular chamber 28, and the rotor 14 is rotated about the stator 12. A carrier liquid 44 is supplied down the duct 30 to the port 32, flowing through the bearing 20 and upwards between the stator 12 and rotor 14 to emerge through the discharge ducts 40. A migrant material is caused to flow down the duct 34 to emerge from the slot 36 into the carrier liquid 44, and is carried upwards through the annular chamber 28. As a result of its passage through the electric field, the migrant is electrophoretically separated into its components, which follow radially separate paths through the chamber 28, and hence emerge through different discharge ducts 40. The flow of carrier liquid 44 and migrant material through the separator 10 is thus fractionated into thirty outlet streams emerging from the thirty ducts 40.

In FIG. 1 the inlet means for the migrant material is represented diagrammatically by the duct 34 and the slot 36. A practical inlet means must provide a smooth and steady flow of migrant material which must emerge in such a manner as not to disrupt the laminar flow of the carrier liquid 44. If, as in FIG. 1, the migrant material emerges from a slot 36 extending completely round the periphery of the stator 12, then the flux of the migrant material should be substantially equal from all parts of the slot 36, and the slot 36 should be sufficiently narrow to produce a well-defined layer of migrant material within the carrier liquid 44 at the lower end of the annular chamber 28.

Figure 2:
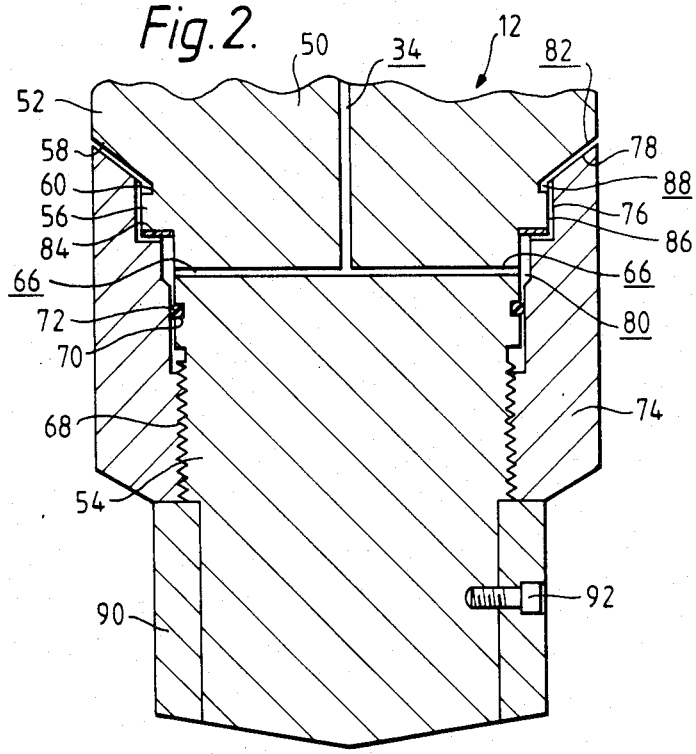
FIG. 2 is a medial sectional view of an inlet means of the electrophoretic separator of FIG. 1.

Referring to FIG. 2, there is shown an inlet means for the electrophoretic separator of FIG. 1. Below the electrode 24 (not shown in FIG. 2) the stator 12 comprises an unplasticised polyvinylchloride (uPVC) generally cylindrical end member 50, with an upper portion 52 of the same diameter as the electrode 24, and a lower portion 54 of smaller diameter. Between the lower portion 54 and the upper portion 52 are a square circumferential step 56 and above that an upwardly sloping conical shoulder 58, there being a circumferential groove 60 between the step 56 and the shoulder 58. The duct 34 for the supply of migrant material extends axially through the end member 50 to communicate with six equally spaced radial holes 66 (only two of which are shown) extending to the surface of the lower portion 54 below the step 56. The duct 30 (see FIG. 1) for the carrier liquid extends through the end member 50 parallel to the axis, and is not in the plane of the Figure.

An intermediate part 68 of the lower portion 54 is threaded, and between the holes 66 and the threaded part 68 is a circumferential groove 70 to locate an O-ring seal 72. A uPVC cylindrical sleeve 74 of the same external diameter as the upper portion 52 fits over the end member 50, engaging with the threaded part 68 and extending between the shoulder 58 and the lower end of the threaded part 68. The internal surface of the sleeve 74 is substantially complementary to the surface of the end member 50, with an upwardly sloping shoulder 78 and a square circumferential step 76, and below the step 76 part of the sleeve 74 is relieved so as to define with the end member 50 an annular chamber 80 with which the holes 66 communicate, the chamber 80 being sealed at its lower end by the O-ring seal 72.

The shoulder 78 is spaced apart from the shoulder 58, so as to define a circumferential slot 82, by a washer 84 between the horizontal parts of the steps 56 and 76. Thirty-six equally spaced shallow grooves 86 extend radially across the horizontal part and axially along the vertical part of the step 76, thus providing communication between the annular chamber 80 and an annular chamber 88 defined by the groove 60 and the sleeve 74.

Below the threaded part 68 the lower portion 54 is of slightly reduced diameter and is covered by a close-fitting cylindrical sleeve 90 of polytetrafluoroethylene (PTFE) held in position by three recessed screws 92 (only one of which is shown). The sleeve 90 bears against the bearing 20 (see FIG. 1).

In operation of the inlet means of FIG. 2, the migrant material is caused to flow down the duct 34, and flows outwardly through the six holes 66 into the annular chamber 80. It then flows through the thirty-six grooves 86 into the annular chamber 88, and through the slot 82 to emerge as a narrow layer into the carrier liquid 44 (see FIG. 1). The slot 82 and the grooves 86 each provide resistance to the flow of migrant material so that there is a steady pressure difference between the chamber 80 and the chamber 88, and between the chamber 88 and the open end of slot 82, and consequently that the flow is substantially the same through each groove 86, and is substantially equal through all parts of the slot 82.

Figure 3:
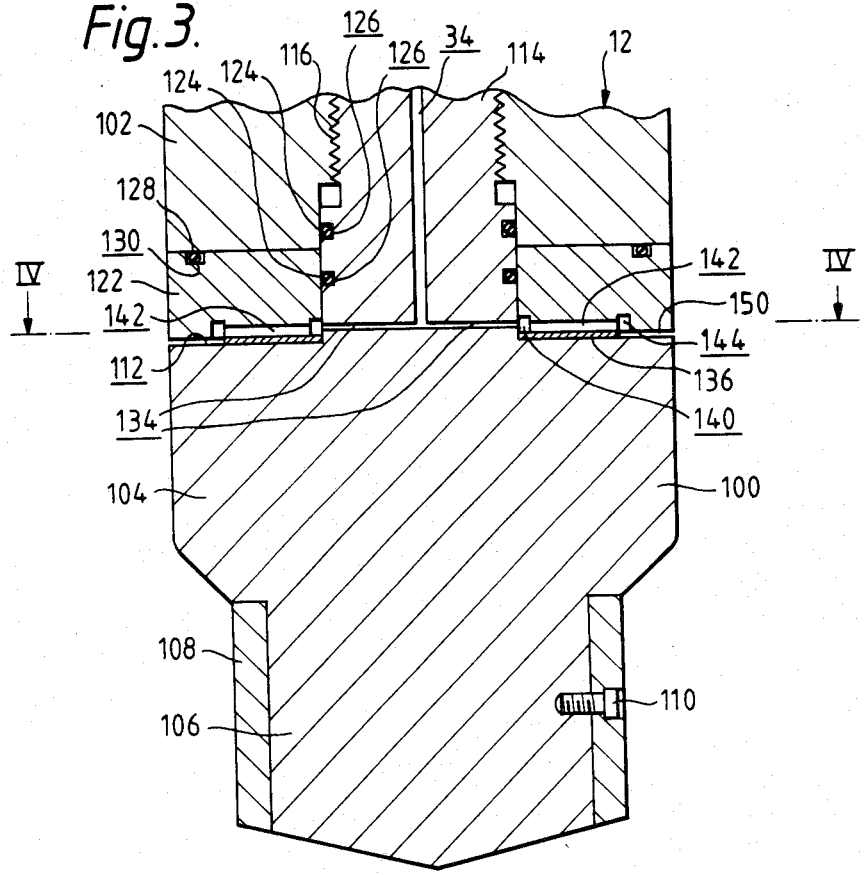
FIG. 3 is a medial sectional view of an alternative inlet means to that of FIG. 2.

It has hitherto been believed that, in view of the proximity of the inlet means to the electrodes 24 and 26 (see FIG. 1), all parts of the inlet means in contact with the migrant material or with the carrier liquid 44 should be made of an electrically insulating material. It was expected that any conducting material near the electrodes 24 and 26 would become electrically polarized by the electric field and therefore bring about electrolysis, with consequent generation of bubbles. Surprisingly it has been found that bubble generation does not occur when parts of the inlet means are of a conducting material such as stainless steel and are electrically insulated from the electrode 24 while the carrier liquid 44 is flowing through the electrophoretic separator 10, and an alternative inlet means for the electrophoretic separator of FIG. 1 is shown in FIG. 3, to which reference is now made, in which the stator 12 includes a stainless steel end member 100 electrically insulated from the electrode 24 (see FIG. 1) by a hollow cylindrical insulating block 102 of Delrin acetal of the same external diameter as the electrode 24. The end member 100 comprises a cylindrical portion 104 of the same diameter as the electrode 24, below which extends a cylindrical portion 106 of smaller diameter covered by a close-fitting tubular Delrin acetal sleeve 108 held in place by three recessed screws 110 (only one of which is shown). The cylindrical portion 104 has a plane upper surface 112 from which extends axially a boss portion 114 of about a third the diameter of the cylindrical portion 104. The upper end 116 of the boss portion 114 is threaded to engage within the hollow insulating block 102, and an annular stainless steel plate 122 of the same external diameter as the cylindrical portion 104 is sandwiched between the block 102 and the surface 112 of the cylindrical portion 104, fitting closely around the lower part of the boss portion 114. Two O-ring seals 124 in grooves 126 around the unthreaded part of the boss portion 114 provide seals between the boss portion 114 and the insulating block 102 and the plate 122 respectively, while an O-ring seal 128 locates in a groove 130 on the upper face of the plate 122 to seal between the plate 122 and the block 102.

Figure 4:
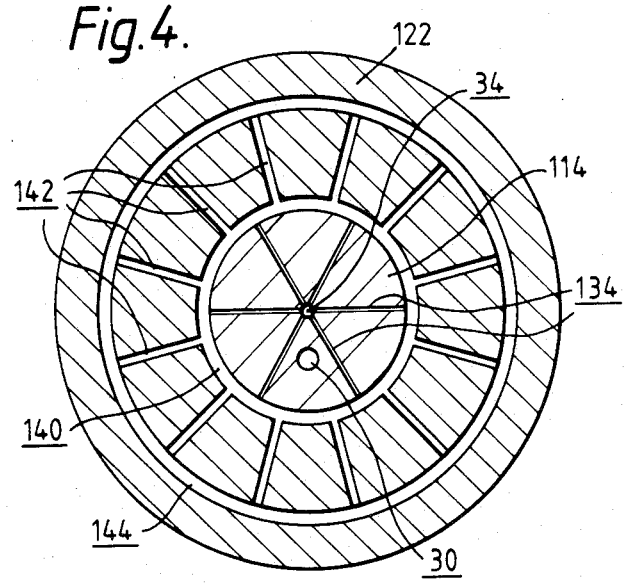
FIG. 4 is a view on the line IV—IV of FIG. 3.

Referring also to FIG. 4, the duct 34 for the migrant material extends axially through the boss portion 114 to communicate with six equally spaced radial holes 134 which extend to the surface of the boss portion 114 about 1 mm above the surface 112. The lower face of the plate 122 is spaced away from the surface 112 by a thin annular washer 136 and is relieved so as to define, in combination with the washer 136 and the boss portion 114, an annular chamber 140 with which the holes 134 communicate. Twelve equally spaced radial grooves 142 in the lower face of the plate 122 extend from the chamber 140 to an annular groove 144 in the lower face of the plate 122, the inside diameter of the groove 144 being the same as the external diameter of the washer 136. A circumferential slot 150 is thus defined between the lower face of the plate 122 and the surface 112, beyond the edge of the washer 136. The width of the slot 150 is defined by the thickness of the washer 136, and is typically chosen to be between 0.15 mm and 0.4 mm depending on the viscosity of the migrant material. The plate 122 is oriented so that the holes 134 are aligned midway between alternate pairs of the grooves 142. The duct 30 (see FIG. 1 and FIG. 4) for the carrier liquid extends through the end member 100 parallel to the axis.

In operation of the inlet means of FIGS. 3 and 4 the migrant material is caused to flow down the duct 34, and flows outwardly through the six holes 134 into the annular chamber 140. It then flows through the twelve grooves 142 into the annular groove 144, and through the slot 150 to emerge as a narrow well-defined layer into the carrier liquid 44 (see FIG. 1). The grooves 142 and the slot 150 each provide resistance to the flow of migrant material so that there is a steady pressure difference between the chamber 140 and the annular groove 144, and between the annular groove 144 and the open end of the slot 150, and consequently that the flow is substantially the same through each groove 142, and is substantially equal through all parts of the slot 150.

In a modified version (not shown) of the inlet means of FIGS. 3 and 4, the part of the surface 112 defining the slot 150 is stepped upwardly to be level with the upper surface of the grooves 142, and the opposed part of the lower surface of the plate 122 is stepped upwardly by the same distance. Consequently the slot 150 is in a plane slightly higher than the plane of the grooves 142, so that after assembling the apparatus and commencing flow of a liquid through the duct 34 any air in the grooves 142 tends to be swept out of the open end of the slot 150.

The use of stainless steel components to define the slot 150, rather than plastics materials such as uPVC, leads to the advantage that the width of the slit 150 is more stable in operation since the thermal expansivity of steel is about a tenth that of plastics materials. Furthermore the components are less prone to be damaged accidently during assembly and disassembly of the electrophoretic separator, and if desired they can be heat-sterilized.

I claim:

1. A continuous flow electrophortic separator comprising a cylindrical stator, a concentric tubular rotor defining an annular chamber between the stator and the rotor, an electrode incorporated in the stator, an electrode incorporated in the rotor, means for causing a carrier liquid to flow through the chamber, and an inlet means in the stator for injecting a migrant material into the carrier liquid, the inlet means defining:
    a supply duct for the supply of the migrant material,
    a first annular chamber,
    a plurality of ducts providing communication between the supply duct and the first annular chamber,
    a circumferential slot around the periphery of the stator,
    a second annular chamber coaxial with the stator and in fluid communication with the slot, and of greater width than the corresponding width of the slot,
    and a plurality of channels providing fluid communication between the first annular chamber and the second annular chamber, the channels being not coplanar with the slot,
so that in use the flux of the migrant material is substantially the same through all parts of the slot.

2. An electrophoretic separator as claimed in claim 1 wherein the number of channels is at least twice the number of ducts, the channels are equally spaced, the ducts are equally spaced, and none of the channels are aligned with the ducts.

3. An electrophoretic separator as claimed in claim 1 wherein the ducts and the channels extend in radial directions and lie in planes perpendicular to the axis of the stator.

4. An electrophoretic separator as claimed in claim 1 wherein the slot lies in a plane perpendicular to the axis of the stator.

5. An electrophoretic separator as claimed in claim 1 wherein the circumferential slot is defined between metal portions of the inlet means.

6. An electrophoretic separator as claimed in claim 1 wherein the slot is of width between 0.15 mm and 0.4 mm.

7. An electrophoretic separator as claimed in claim 1 wherein the inlet means comprises:
    (a) a stainless steel end member of generally cylindrical shape, defining a plane annular end surface and a central cylindrical boss, the supply duct and the ducts being defined within the said end member and the ducts emerging from the boss adjacent the plane end surface;
    (b) an annular washer located around the boss and of smaller external radius than the said plane end surface; and
    (c) a stainless steel annular member close-fitting about the boss, having a plane surface of the same external radius as the said plane end surface spaced apart from the said plane end surface by the washer, in which plane surface are defined an annular recess adjacent the boss to define the first annular chamber, an annular groove to define the second annular chamber, and a plurality of radial grooves between the recess and the annular groove to define the channels, a gap between peripheral portions of the plane end surface and of the plane surface outside the washer defining the circumferential slot.

* * * * *